United States Patent [19]

Castleman et al.

[11] 4,075,550
[45] Feb. 21, 1978

[54] IONIZATION CELL FOR SENSING AND MEASURING GASEOUS IMPURITIES

[75] Inventors: B. Wayne Castleman, Largo; Bernard C. Schluter, Clearwater, both of Liechtenstein

[73] Assignee: Honeywell Inc., Minneapolis, Minn.

[21] Appl. No.: 754,148

[22] Filed: Dec. 27, 1976

[51] Int. Cl.² .......................................... G01N 27/00
[52] U.S. Cl. .................... 324/33; 73/194 F; 250/308
[58] Field of Search ........................ 324/33; 73/194 F; 250/308, 432, 435

[56] References Cited

U.S. PATENT DOCUMENTS

| | | | |
|---|---|---|---|
| 3,317,823 | 5/1967 | Brodsky | 324/33 |
| 3,648,517 | 3/1972 | Dorman | 73/194 F |
| 3,835,328 | 9/1974 | Harris et al. | 73/194 F X |
| 4,019,383 | 4/1977 | Wiegand, Jr. et al. | 73/194 F |

*Primary Examiner*—Rudolph V. Rolinec
*Assistant Examiner*—Vincent J. Sunderdick

*Attorney, Agent, or Firm*—Albin Medved

[57] ABSTRACT

An improved gas ionization cell with compensation for variations in flow rate of the gas and variations in radioactive source intensity. A gas sample is directed past a source of ionizing radiation and through a recombination region to an ion collection screen, where output current is monitored to give an indication of trace gases or vapors present in the gas under surveillance. Compensation for changes in gas flow rate and source intensity is provided by taking a portion of the gas subjected to the ionizing radiation and directing that portion of the gas through a channel by-passing the recombination region of the cell and past a pair of conductive probes. The first probe of the pair is biased at a predetermined voltage, while electric current is monitored at the second probe spaced downstream from the first probe. The current generated at the second probe, which is for all practical purposes a function of only the rate of gas flow and the source intensity, provides the compensation signal for the ionization cell.

4 Claims, 8 Drawing Figures

IONIZATION CELL FOR SENSING AND MEASURING GASEOUS IMPURITIES

CROSS-REFERENCE TO RELATED APPLICATION

The subject matter of this specification is related to application Ser. No. 736,627, filed in the U.S. Patent and Trademark Office on Oct. 28, 1976.

BACKGROUND OF THE INVENTION

The present invention relates to ionization cells of the type generally described in U.S. Pat. No. 3,835,328. Such cells can be used to detect the presence of very small concentrations of a select group of chemical vapors or gases in the air or in other vapor or gas backgrounds. Described in U.S. Pat. No. 3,835,328, is an ionization detector in which a gas sample flows past a source of ionization radiation and through a recombination region to an ion collection region, where a current is produced as a function of the ion concentration in the gas sample. By providing a sufficiently long path and an exposure to adequate surface, the recombination of ions is enhanced and controlled in such a way that ion concentration remaining in the gas sample when it reaches the collection region is a function of trace gases or vapors in the sample.

Deficiencies in the prior art design of ionization cells are that a variation in the rate of gas flow and/or a variation in the intensity of the ionizing radiation will result in a corresponding change in the concentration of ions reaching the collection region of the cell. To assure that the current monitored at the collector screen mounted in the collection region of the cell is a function of trace gases or vapors only, it is required that a very good constant rate pump be used to maintain a constant flow rate, or alternatively, that compensation be provided to correct for errors caused by changes in flow rate. In addition, compensation should be provided for a decrease in the intensity of the ionizing radiation due to natural radioactive decay and other factors, such as contaminating films. In the prior art, compensation flow rate changes are provided by utilizing a separate means for detecting flow changes, such as by using a second ionization cell sensitive only to flow changes. No compensation was provided in the prior art for source degradation.

SUMMARY OF THE INVENTION

In accordance with the present invention, a single ionization cell is utilized to provide the sensing features of the ionization cell and to also provide a signal which is proportional to the flow rate of the gas sample and to the ionizing radiation source intensity. This is accomplished by taking a portion of the gas sample, after it has been exposed to the ionizing radiation, and directing this portion of the gas sample past a pair of flow probes through a channel which by-passes the recombination region of the cell. The signal generated at the flow probes is proportional to the gas flow rate and the ionizing radiation source intensity. This signal is combined with the signal generated at the collector screen of the ionization cell, which is a function of the concentration of the trace gas or vapor. The flow rate and source signal is used to compensate for variations in the ionization cell output caused by variations in the rate of the gas flow and source intensity.

A number of significant advantages are obtained by the improved design of the present invention. By using the same ionizing source for both the detection of trace gases or vapors and detection of flow rate and source intensity changes, errors due to non-uniform ionizing source decay of two separate cells is eliminated. Further advantage of the improved ionization cell described herein is that only a single cell is required to provide both the sensing signal and flow and source compensation. As a result, the size and the power requirements of the cell can be reduced.

DESCRIPTION OF THE PREFERRED EMBODIMENT

Figure 1:
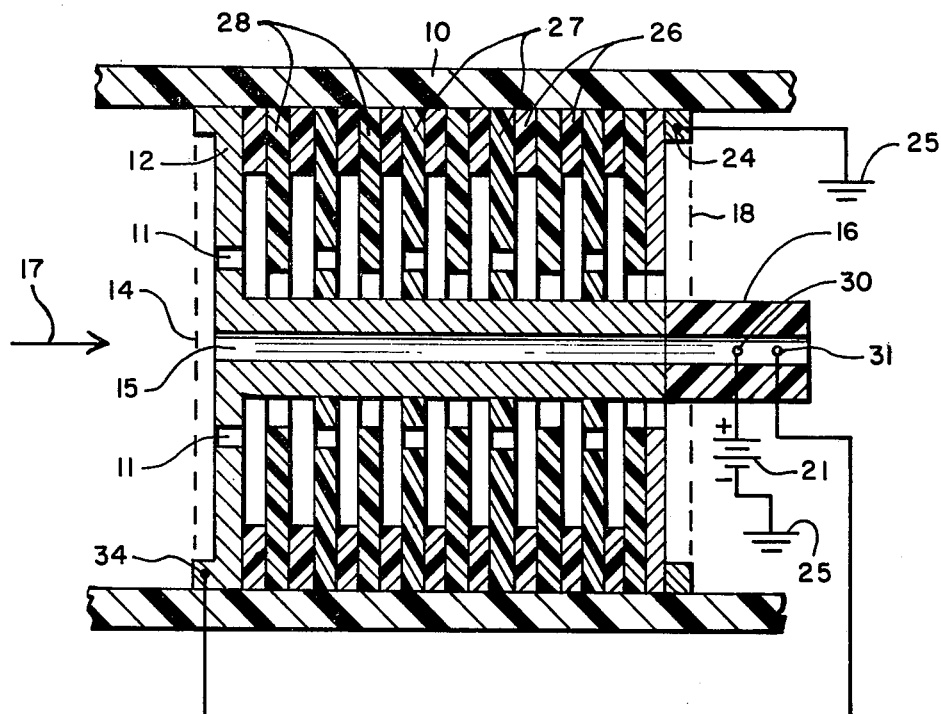
FIG. 1 shows a cross-sectional view of an ionization cell with a compensation arrangement according to the present invention, including a schematic representation of the associated electrical components and connections.
Figure 1:
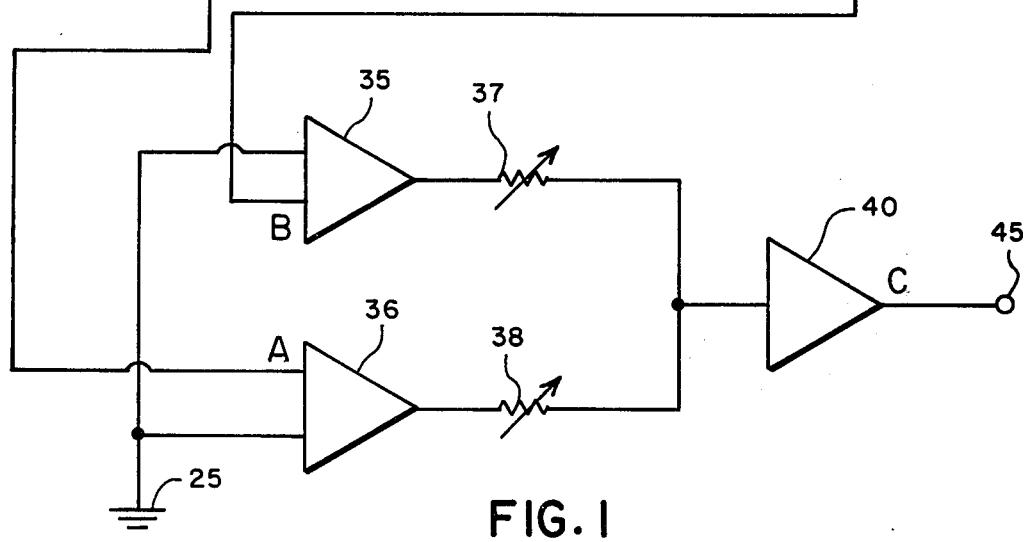

Referring to FIG. 1, the preferred embodiment of the apparatus includes a housing 10 constructed of a non-conductive material, such as Teflon. Mounted within the housing, at a first end, is a radiation emitting source 14, which consists of a metal screen to which is affixed a radiation emitting foil. A manifold 12, constructed of a conductive material, and consisting of a circular flange corresponding in size to the internal cross-sectional dimension of housing 10, and a metal stud protruding from the flange axially along housing 10, is positioned adjacent to radiation emitting source 14. Manifold 12 has an axial bore along the longitudinal axis of the metal stud, forming a channel for flow of gas from radiation source 14 at the first end of housing 10, to the other end of housing 10. The flange portion of manifold 12 further contains a number of apertures 11, which provide the passages for gas from radiation source 14 into a recombination region.

Gas sample, such as air, enters housing 10 as shown by arrow 17, impinging on radiation source 14, where the gas is ionized. Beyond source 14, the gas enters a recombination region through apertures 11 in manifold 12. A portion of the gas sample also flows into channel 15 in the manifold stud, which serves as a conduit to allow a portion of the gas sample to by-pass the recombination region. The recombination region includes a series of washers 26 and baffles 27 and 28, as shown in FIG. 1, and as described in U.S. Pat. No. 3,835,328. The series of washers and baffles provide an extended path which enhances ion recombination by exposing ions to large surface area. The washers and baffles of the recombination region are constructed of a non-conductive material, such as Teflon.

Adjacent to the downstream end of the recombination region is mounted a collector screen 18, which is connected electrically to a ground potential terminal 25. Terminal 25 can be either grounded as shown or have a voltage applied to the terminal with the magnitude and polarity of the voltage dependent upon the function of the sensor. The current generated by the non-recombined ions remaining in the gas emerging from the recombination region and impinging on collector 18 is monitored between collector screen 18 and conductive manifold 12. The electrical signal is taken from manifold 12 at terminal 34 and is applied to the input A of an amplifier 36. Amplifier 36 has its second input connected to ground terminal 25.

A characteristic of an ionization cell, as described above, is that the signal from the cell is a function of both the composition of the gas flowing through the cell, as well as the flow rate of the sample of gas and the intensity of the radioactive source. To provide a signal to compensate for the variations in the flow rate of the gas and intensity of the source, a portion of the ionized gas is directed through channel 15 of the manifold stud, by-passing the recombination region of the cell. This gas sample is directed past a pair of electrical probes 30 and 31 located in an extension 16 of the manifold stud. Probes 30 and 31 are positioned in a spaced relationship, probe 31 being located downstream from probe 30. Extension 16 of the manifold stud is constructed of a non-conductive material such as Telfon to isolate probes 30 and 31 electrically from manifold 12. Probe 30 is connected to a positive source of potential 21, whose negative end is connected to ground terminal 25. The compensating signal is taken at probe 31 and applied to input B of an amplifier 35, which has a second input connected to ground terminal 25.

Figure 4:
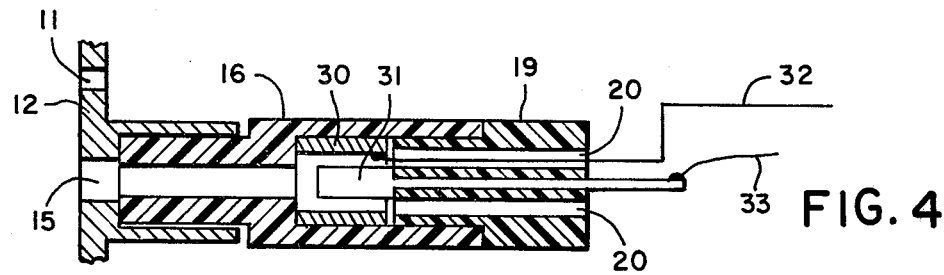
FIG. 4 is an alternate arrangement of the electrical probes for generating a flow rate signal.

An alternate arrangement of electric probes 30 and 31 for generating a flow rate signal is shown in FIG. 4. The reference numerals in FIG. 4 are the same as those identifying the corresponding elements in FIG. 1. Electric probe 30 is formed in a cylindrical shape, while electric probe 31 is in the form of a pin positioned inside and coaxial with probe 30. Probe 31 is held in place by a second Teflon insert 19. Insert 19 has a plurality of passages 20, through which the gas moves after it flows past probes 30 and 31. Electric conductors 32 and 33 connect probes 30 and 31 to source of potential 21 and amplifier 35, as shown in FIG. 1. An advantage of the arrangement shown in FIG. 4 is that it requires lower potential between probes 30 and 31.

Figure 2A:
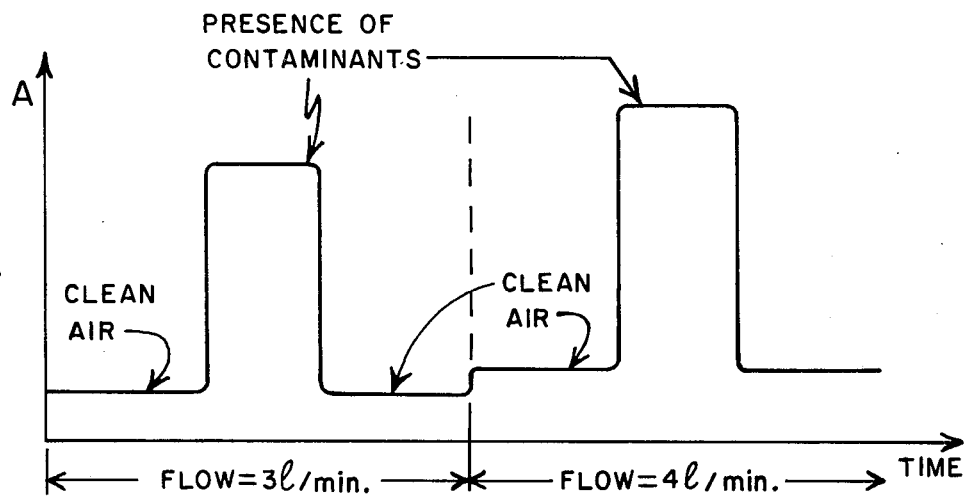
FIG. 2 (a-c) is a graphic representation of electrical signals generated at various points of the apparatus of FIG. 1 in response to different rates of gas flow.

FIG. 2A illustrates a typical signal appearing at the output of the ionization cell as appearing at input A of amplifier 36. The signal shown in responsive to a gas comprised of clean air followed by introduction of contaminants. The left half of the curve represents a signal responsive to a flow rate of 3 liters per minute while the right half of the curve represents a signal responsive to a flow rate of 4 liters per minute, the proportion of contaminants being constant.

Figure 2B:
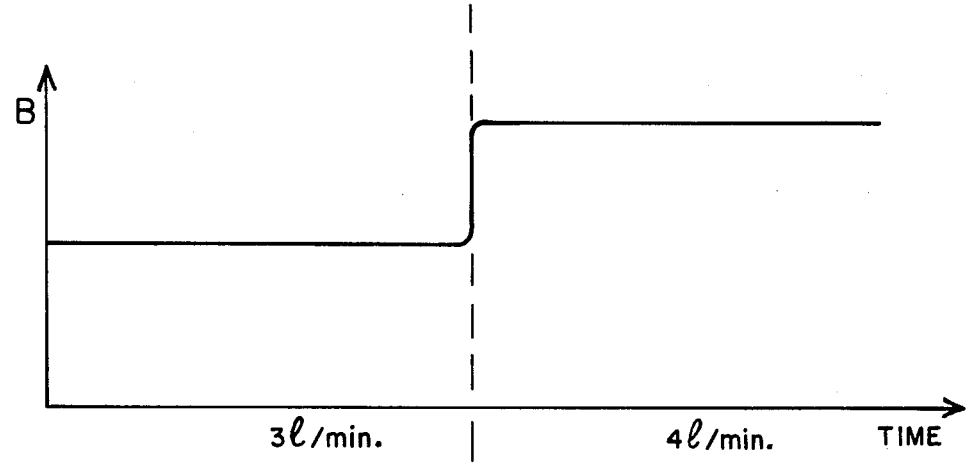
Figure 2C:
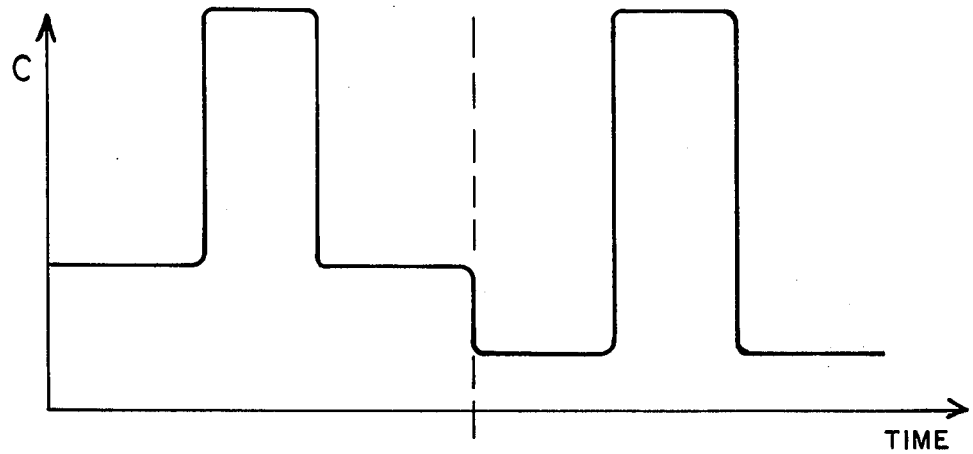

In FIG. 2B the signal appearing at probe 31 and input B of amplifier 35 is shown. Again, the left half of the curve represents a signal responsive to a flow rate of 3 liters per minute, while the right half represents a signal responsive to a flow rate of 4 liters per minute. It has been shown experimentally that by by-passing the recombination region of the cell, a significant recombination of ions has not occurred in the sample directed past probes 30 and 31 and the signal detected is substantially a function of only the carrier gas. The changes in signal amplitude between the left and the right halves of the curve are due only to the change in the rate of gas flow. By combining signals A and B, as shown in FIG. 1, and by properly adjusting gain adjustment resistors 37 and 38, the changes in the cell output signal due to gas flow rate are compensated. The compensated signal C appearing at output 45 of amplifier 40 is shown in FIG. 2C.

Figure 3A:
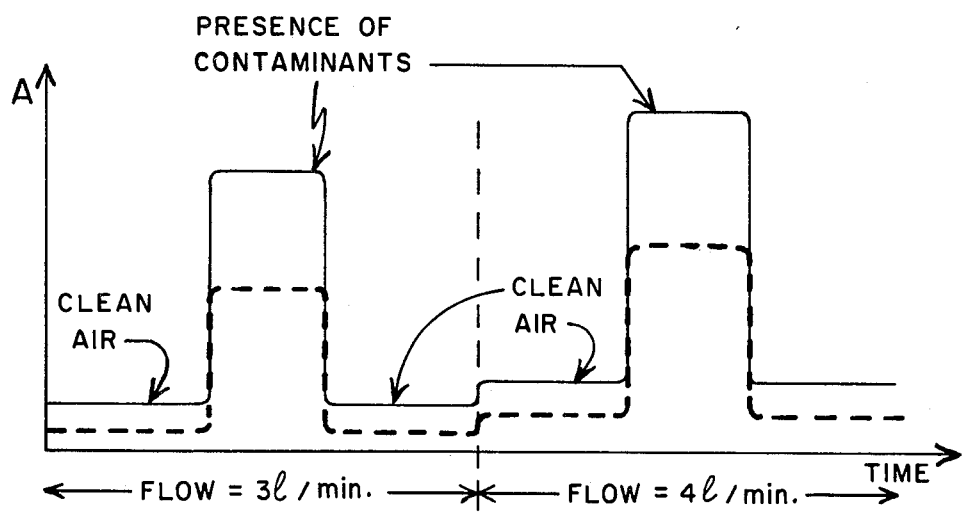
FIG. 3 (a-c) is a graphic representation of electrical signals generated at various points of the apparatus of FIG. 1 in response to different rates of gas flow and different radiation source intensities.
Figure 3B:
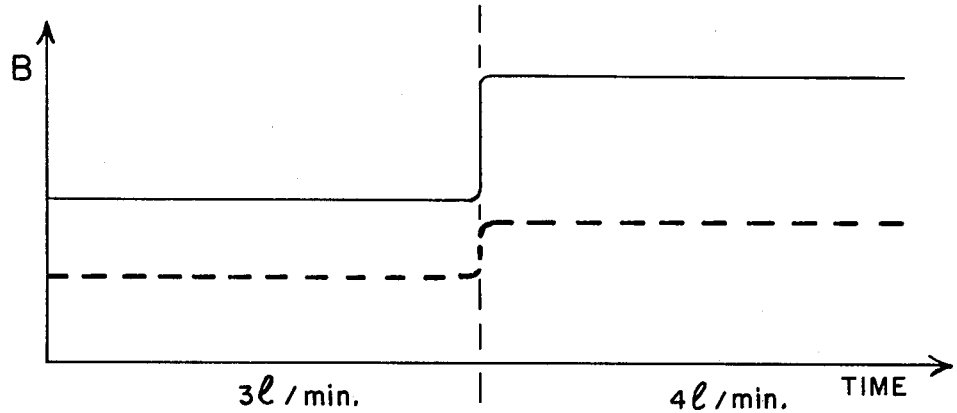
Figure 3C:
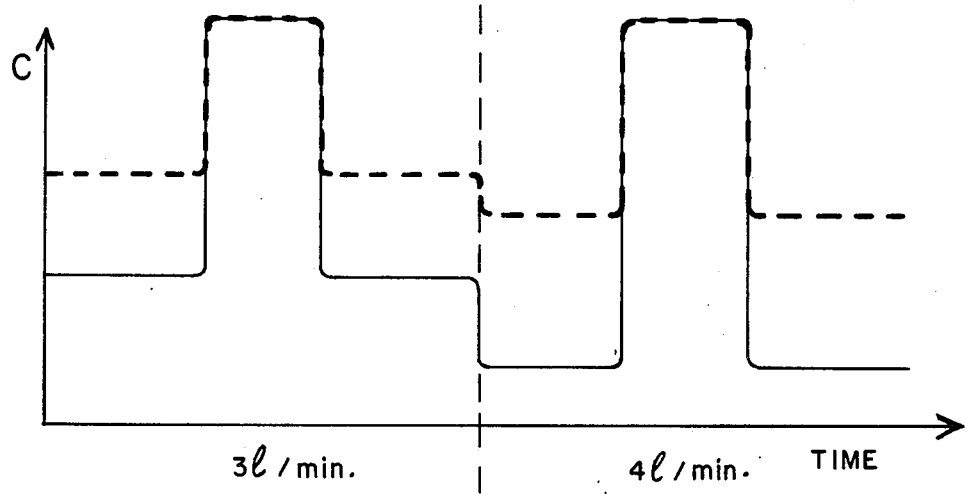

The solid lines of FIG. 3 show the same signals as described in FIG. 2. The dashed lines in FIG. 3 show the signals from the same clean air and proportion of contaminants following decay or contamination of the radioactive source. FIG. 3A illustrates that the magnitude of the signals for both clean air and contaminants is decreased because of decreased source intensity. FIG. 3B illustrates that the signal from probe 31 is also decreased proportionately to the signal of FIG. 3A. FIG. 3C shows that when appropriately combined, the signals from the dotted lines in FIGS. 3A and 3B have the same magnitude when contaminants are present as when the source was at its original intensity (solid lines), and thus source compensation is provided.

A unique and improved ionization cell for sensing and measuring gaseous impurities has been shown and described in the foregoing specification. Various modifications of the inventive concept will be obvious to those skilled in the art, without departing from the spirit of the invention. It is intended that the scope of the invention be limited only by the following claims.

What is claimed is:

1. An ionization detector with compensation means for variations in the flow rate of gas sample through the detector and for variations in the ionizing radiation source intensity, comprising:

a housing having an input and an output for flow of gas therethrough;

a source of ionizing radiation positioned in said housing in the proximity of said input;

an electrically conductive manifold mounted within said housing adjacent said source of ionizing radiation on the side nearer said output, said manifold constituting a partition within said housing separating said source of ionizing radiation from a recombination region, said manifold further having a plurality of apertures to permit gas flow from the input of said housing, past said ionizing radiation, into said recombination region;

a collector electrode mounted near the output of said housing for generating a first electric signal which is a function of the number of ions present in the gas after passing through said recombination region;

a conduit connected to said manifold, said conduit providing a passage by-passing said recombination region for a portion of said gas ionized by said radiation source;

first and second electric probes mounted in the passage of said conduit for generating a second electric signal which is a function of the number of ions present in the portion of said gas not passing through the recombination region; and means for utilizing said second signal to compensate for variations in said first signal caused by variations in the rate of gas flow and/or variations in intensity of said source of ionizing radiation.

2. Apparatus according to claim 1, wherein said first and second electric probes are, respectively, in the shape of a cylindrical ring and a pin positioned axially with respect to said cylindrical ring and also with respect to said passage in said conduit.

3. Apparatus according to claim 1, said apparatus further including:

a first amplifier having an input connected to receive said first electric signal, and having an output;

a second amplifier having an input connected to receive said second electric signal, and having an output; and means for combining the signals appearing at the outputs of said first and second amplifiers in a manner to utilize the signal from the second amplifier to compensate for variations in the signal from said first amplifier caused by variations in the rate of gas flow and/or variation in intensity of said source of ionizing radiation.

4. Apparatus according to claim 3, wherein said first electric probe is connected to a source of electric potential and said second electric probe is connected to the input of said second amplifier.

* * * * *